(12) United States Patent
Stahl

(10) Patent No.: US 11,612,581 B2
(45) Date of Patent: Mar. 28, 2023

(54) CANNABIS AND DERIVATIVES THEREOF FOR THE TREATMENT OF PAIN AND INFLAMMATION RELATED WITH DENTAL PULP AND BONE REGENERATION RELATED TO DENTAL JAW BONE DEFECTS

(71) Applicant: CANNIBITE BVBA, Mortsel (BE)

(72) Inventor: Veronica Stahl, Mortsel (BE)

(73) Assignee: Cannibite BVBA

( * ) Notice: Subject to any disclaimer, the term of this patent is extended or adjusted under 35 U.S.C. 154(b) by 205 days.

(21) Appl. No.: 16/637,533

(22) PCT Filed: Aug. 9, 2018

(86) PCT No.: PCT/IL2018/050885
§ 371 (c)(1),
(2) Date: Feb. 7, 2020

(87) PCT Pub. No.: WO2019/030762
PCT Pub. Date: Feb. 14, 2019

(65) Prior Publication Data
US 2020/0222361 A1 Jul. 16, 2020

Related U.S. Application Data

(60) Provisional application No. 62/542,846, filed on Aug. 9, 2017.

(51) Int. Cl.
*A61K 31/352* (2006.01)
*A61K 31/05* (2006.01)
*A61K 9/00* (2006.01)
*A61P 1/02* (2006.01)

(52) U.S. Cl.
CPC .......... *A61K 31/352* (2013.01); *A61K 9/0019* (2013.01); *A61K 9/0053* (2013.01); *A61K 31/05* (2013.01); *A61P 1/02* (2018.01)

(58) Field of Classification Search
CPC .................................................. A61K 31/352
See application file for complete search history.

(56) References Cited

U.S. PATENT DOCUMENTS

| | | |
|---|---|---|
| 6,903,137 B2 | 6/2005 | Fride et al. |
| 7,214,716 B2 | 5/2007 | Fride et al. |
| 7,235,584 B2 | 6/2007 | Garzon et al. |
| 2007/0197509 A1* | 8/2007 | Babinski ............ A61K 31/517 546/159 |
| 2008/0103193 A1 | 5/2008 | Castor et al. |
| 2008/0139667 A1 | 6/2008 | Robson et al. |
| 2009/0136893 A1 | 5/2009 | Zegarelli |
| 2009/0148486 A1 | 6/2009 | Lu et al. |
| 2016/0166498 A1 | 6/2016 | Anastassov et al. |
| 2022/0323323 A1* | 10/2022 | Stahl ................... A61K 8/8176 |

FOREIGN PATENT DOCUMENTS

| | | |
|---|---|---|
| CA | 2859930 A | 3/2016 |
| CN | 105998958 A | 10/2016 |
| EP | 2044935 A1 | 4/2009 |
| WO | 2011063164 A2 | 5/2011 |
| WO | 2015168292 A1 | 11/2015 |

OTHER PUBLICATIONS

Xie, Yun. "Killing bacteria with cannabis." J. Nat. Prod. (2008). Accessed Feb. 19, 2022. Available from: < https://arstechnica.com/science/2008/08/killing-bacteria-with-cannabis/ > . (Year: 2008).*
International Search Report, dated Jan. 29, 2019, International Application No. PCT/IL2018/050885.
Somsak Mitrirattanakul, et al., Cannabinoid Receptor 1 (CB1R) Expression in Rat Dental Pulp, Oral Science International, vol. 9, 2012, 17-20.
TAU Researcher: Cannabis Can Help Heal Bone Fractures, Tel Aviv University, Jul. 21, 2015, https://english.tau.ac.il/news/cannabis_heal_bone_fractures.

* cited by examiner

*Primary Examiner* — John S Kenyon
(74) *Attorney, Agent, or Firm* — McAndrews, Held & Malloy, Ltd.

(57) ABSTRACT

The present invention discloses a cannabinoid-based composition useful for treating or preventing dental pulp associated diseases. The composition comprises an effective amount of *Cannabis* extract or a derivative thereof or at least one synthetic cannabinoid for the treatment of dental pulp inflammation, pulp infection and/or dental bone defects. The present invention further discloses methods for treating or preventing dental pulp associated diseases.

10 Claims, 12 Drawing Sheets

- Caries, toxins/bacterial stimulus
- Chemical stimulus
- Thermal stimulus
- Mechanical stimulus

- Pulpal canal changes

- Higher intra canal pressure

- Pulp death

- Necrosis

- Periapical lesion

Figure 3

CANNABIS AND DERIVATIVES THEREOF FOR THE TREATMENT OF PAIN AND INFLAMMATION RELATED WITH DENTAL PULP AND BONE REGENERATION RELATED TO DENTAL JAW BONE DEFECTS

CROSS-REFERENCE TO RELATED APPLICATIONS

The present application is a National Phase Entry of PCT International Application No. PCT/IL2018/050885 which was filed on Aug. 9, 2018, which claims priority to provisional patent application S.N. 62/542,846, filed Aug. 9, 2017, both of which are hereby incorporated by reference in their entireties.

FIELD OF THE INVENTION

The present invention generally pertains to the use of Cannabis extracts and derivatives thereof (THC, CBD) or synthetic cannabinoid for the treatment of pain, inflammation related to dental pulp and bone regeneration related to jaw bone defects. The present invention further pertains to means and methods for treating pain, inflammation and bone defect conditions in dentistry.

BACKGROUND OF THE INVENTION

The dental pulp is the center of the tooth, consisting of living connective tissue and cells and is a part of the denting-pulp complex (endodontium).

The pulp comprises a central pulp chamber, pulp horns and radicular pulp. A large mass of pulp is contained within the pulp chamber, itself contained in and mimics the overall shape of the crown of the tooth. The pulp chamber becomes smaller with age due to the of continuous deposition of dentin Accessory canals (also called lateral canals) are pathways from the radicular pulp, extending laterally through the dentin to the periodontal ligament seen especially in the apical third of the root.

The primary function of the dental pulp is to form dentin (by the odontoblasts) but other functions include: nutritive, sensory and protective. The cellular population of dental pulp includes fibroblasts (the principal cells), odontoblasts, and defense cells such as histiocytes, macrophage, granulocytes, mast cells and plasma cells. The nerve plexus of Raschkow is located central to the cell-rich zone and monitors painful sensations/playing an important part in inflammation and tissue repair.

Pulpitis is the inflammation of the pulp and can be extremely painful and in severe cases requires root canal therapy/endodontic therapy. Iritated pulp starts an inflammatory response but due to the hard and closed surroundings of the pulp, pressure builds inside the pulp chamber hyperemia compressing the nerve fibers and eliciting extreme pain (acute pulpitis). At this stage the death of the pulp begins, which can progress to periapical abscess formation (chronic pulpitis). Pulpitis is mainly caused by bacterial infection, itself is a secondary development of tooth decay, manifesting in the form of a toothache. Increased sensitivity to stimuli, specifically hot and cold, is a common symptom of pulpitis. A prolonged throbbing pain may be associated with the disease. However, pulpitis can also occur without any pain. Once the pulp has become inflamed, the tooth can be diagnostically divided into two categories:

Reversible pulpitis is the condition where the pulp is still considered to be vital, meaning that once the irritant is eliminated, usually by removal of decay and the placement of a restoration, the pulp will recover to its normal, healthy state.

Irreversible pulpitis is the condition where the pulp is still alive, but the introduction of bacteria into the pulp will not allow the pulp to heal, ultimately resulting in necrosis of the pulp tissue. Symptoms associated with irreversible pulpitis may include dull aching, pain from hot or cold (though cold may actually provide relief) lingering pain after removal of a stimulus, spontaneous pain, or referred pain. The clinical signs may include reduced response to electronic pulp testing, pulse oximetry and thermal stimuli.

The general viewpoint in dentistry is that the pulp of a tooth with irreversible pulpitis must be treated, with the conventional wisdom being that it is preferable to have a trouble-free (dead) tooth. The tooth may be endodontically treated whereby the pulp is removed and replaced by gutta percha and sealer material. An alternative is extraction of the infected tooth if a large periapical lesion is involved or if there is insufficient coronal tissue remaining for restoration once the root canal therapy has been completed or complications of the bifurcation region and large lesions.

US20080103193 discloses prodrug compositions comprising DELTA.9-tetrahydrocannabinol (.DELTA.9-THC) and .DELTA.9-tetrahydrocannabinolic acid (.DELTA.9-THCA), and methods for the treatment of pain and cachexia or AIDS. US20170027978 teaches a composition for treating pain comprising: (i) tetrahydrocannabinol (THC); (ii) cannabidiol (CBD); and (iii) cobalamin.

CA2859930 discloses a topical composition whereby a 50:50 mixture of Cannabis Indica and Sativa is extracted with heated coconut oil (146-149° C.) and cooled to congealing (28° C.).

CN105998958 discloses a medicine for treating pancreatic cancer.

U.S. Pat. Nos. 7,214,716 and 6,903,137 relate to pharmaceutical compositions comprising as the active ingredient 4-phenyl pinene derivatives which are specific for the peripheral cannabinoid receptors binding selectively to CB2.

U.S. Pat. No. 7,235,584 discloses non-psychotropic cannabinoids and pharmaceutical compositions comprising these compounds for preventing neurotoxicity, neuroinflammation, immune or inflammatory disorders comprising as active ingredient the stereospecific (+) enantiomer, having (3S,4S) configuration of Delta<6>tetrahydrocannabinol type compounds.

A study conducted on rats with mid-femoral fractures reports that the administration of the non-psychotropic component cannabinoid cannabidiol (CBD) enhances bone fractures healing after eight weeks (Jul. 16, 2015, American Friends of Tel Aviv University).

EP2044935 relates to a composition comprising cannabidiol and Denbinobin and its use for the prevention and treatment of gastrointestinal inflammatory diseases and for the prevention and treatment of gastrointestinal cancers.

"Cannabinoid receptor 1 (CB1R) expression in rat dental pulp", Mitrirattanakula S. et al, Oral Science International, Volume 9, Issue 1, May 2012, Pages 17-20 reported that CB1R immunoreactivity (CB1R-ir) was observed to be associated with nerve fibers in radicular pulp and was seen as a continuous network in the subodontoblastic layer.

None of the above mentioned documents provide a solution for the treatment and prevention of diseases and conditions associated with dental pulp inflammation, infection, and pain and/or jaw bone defects, showing there is an unmet long felt need for an anti-inflammatory and anti-bacterial composition for effectively treating and preventing diseases and conditions associated with dental pulp.

SUMMARY OF THE INVENTION

Various objects of the invention are hereby presented in a non-limiting manner: An object of the invention is to disclose cannabinoid-based compositions useful for treating dental pulp associated diseases, wherein the composition comprises an effective amount of *Cannabis* extract or a derivative thereof or at least one synthetic cannabinoid for the treatment of dental pulp inflammation, dental pulp infection and/or dental bone defects. Another object of the invention is to disclose methods of treating dental pulp associated diseases and/or dental bone defects, wherein the method comprises steps of administering a composition as defined in any of the above.

BRIEF DESCRIPTION OF THE FIGURES AND IMAGES

Exemplary embodiments are illustrated in referenced figures. It is intended that the embodiments and figures disclosed herein be considered as being illustrative, rather than restrictive. The disclosure, however, both as to organization and method of operation, together with objects, features, and advantages thereof, may best be understood by reference to the following detailed description when read with the accompanying figures, in which:

FIG. 1 presents a schematic representation of dental pulp anatomy.

FIG. 2 schematically illustrates the Brännström's hydrodynamic theory in dentistry.

FIG. 3 schematically illustrates a flowchart describing pulpal inflammation process, according to certain embodiments of the present invention.

FIG. 4 schematically illustrates aspects of dental pulp pathology.

FIG. 5 schematically illustrates acute pulpitis, chronic pulpitis and necrosis features.

Figure 12:
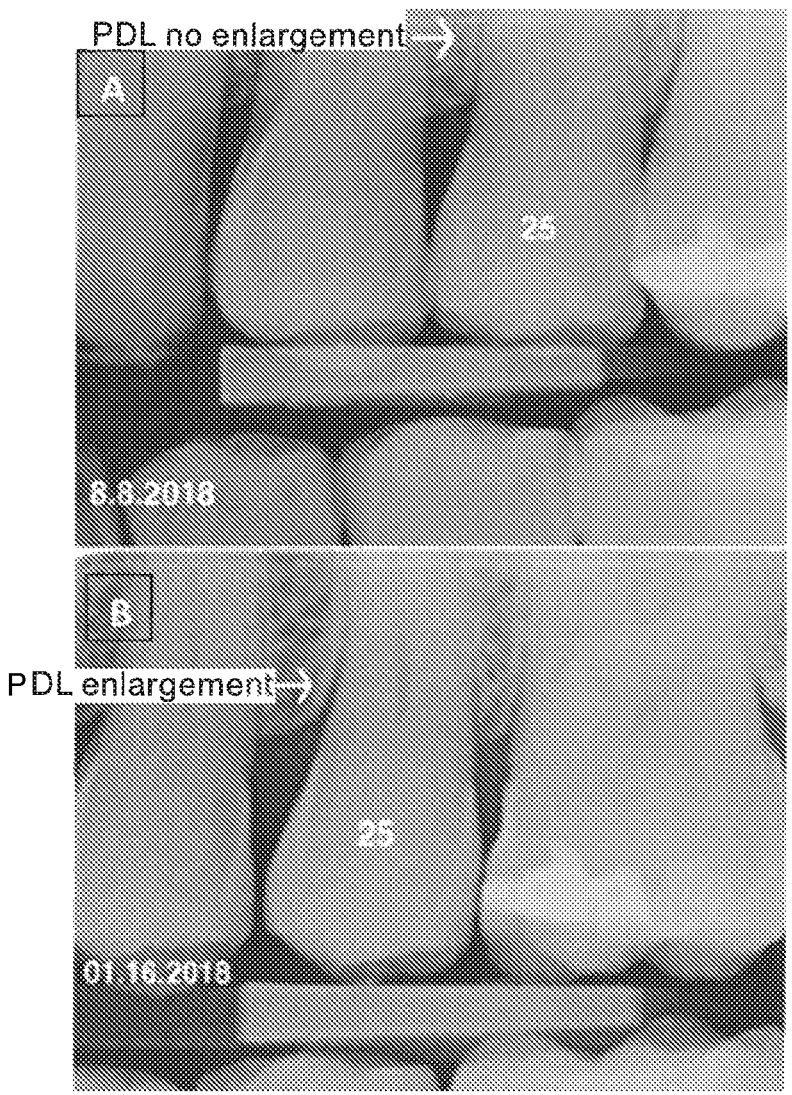
FIG. 12 is an X ray photograph of Patient A before anti inflammation treatment (A) and approx. 8 months after anti-inflammation application of CBD oil 25%+1% THC during 1 week at the tooth neck zone (B).
Figure 13:
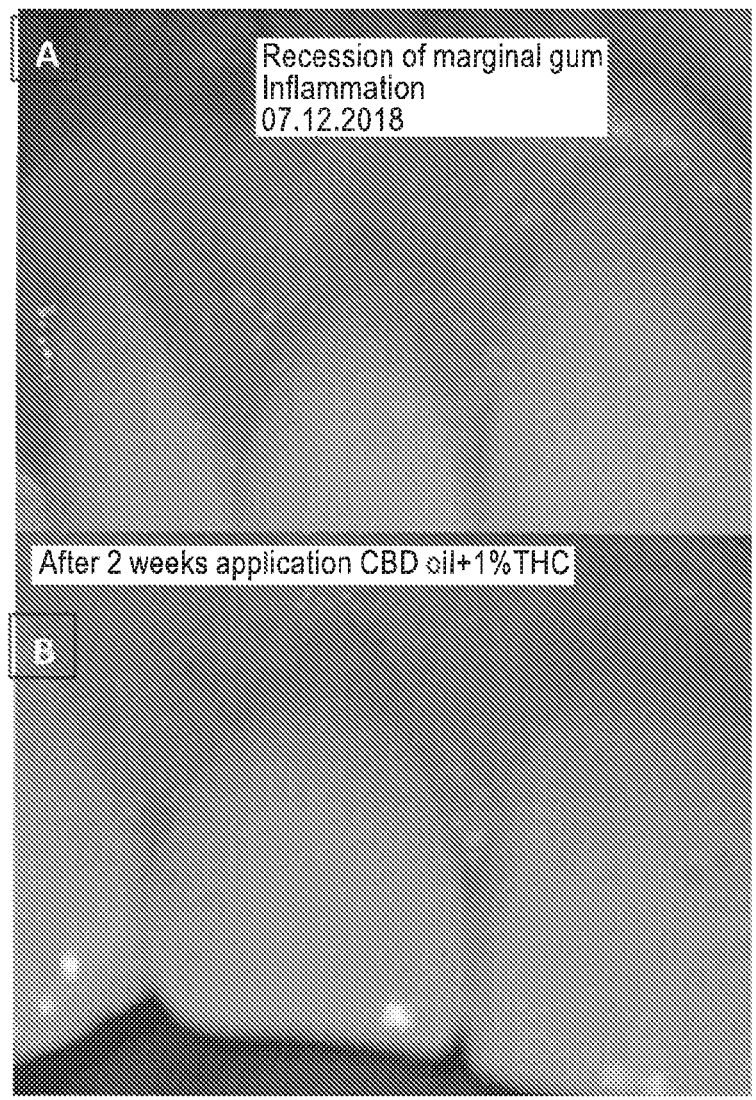
FIG. 13 is an X ray photograph of a Patient B before anti inflammation treatment (A) and (B) after anti inflammation treatment with of CBD oil 25%+1% THC.
Figure 14:
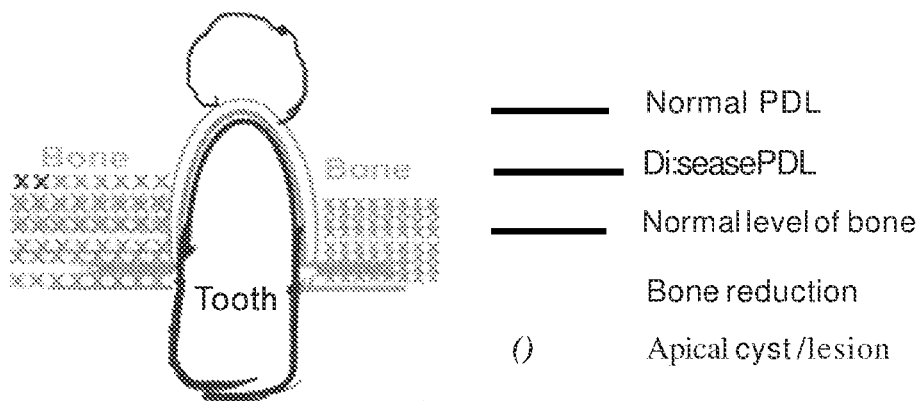

FIG. 14 schematically illustrates the figures FIGS. 12 and 13.

DETAILED DESCRIPTION OF PREFERRED EMBODIMENTS

The following description is hence provided, so as to enable any person skilled in the art to make use of the invention and sets forth the best modes contemplated by the inventor of carrying out this invention. Various modifications, however, are adapted to remain apparent to those skilled in the art, since the generic principles of the present invention have been defined specifically to provide *Cannabis* extracts and derivatives thereof (THC, CBD) or at least one synthetic cannabinoid for the treatment of pain and/or inflammation related to dental pulp and/or bone defects related dental pulp disease complications and/or jaw bone defects.

A major cause of inflammation in human dental pulp is the presence, in the affected dentine, of the oral bacteria responsible for carious lesion development. Pulp inflammation accompanies the host's innate and adaptive immune responses to these bacteria and/or to their components released during bacterial growth that diffuse to the pulp through dentine tubules. It generally reduced after pathogen removal by the dental practitioner and neutralization of diffusing components by the pulp immune system, which both decrease the production of pro-inflammatory mediators. However, in cases of significant dentine damage, pulp inflammation does not resolve completely but becomes chronic with moderate inflammatory infiltrate, collagenous fibrosis and premature tissue aging, and sometimes leads to pulp necrosis and dental abscess development. These evolutions induce permanent loss of normal tissue function and reduction of pulp defense capacities to future injuries. Conversely, cessation of pulp inflammation generally induces the re-establishment of homeostasis and accurate tissue healing characterized by maintenance of pulp vitality, absence of inflammatory infiltrate and fibrosis, and formation of a barrier of reactionary dentine by surviving original odontoblasts and/or reparative dentine by newly differentiated odontoblast-like cells. Dentine neoformation moves the pulp tissue away from the dentine injury and the crown filling biomaterial, thus reducing the risk of permanent irritation by external chemical or bacterial agents. It is acknowledged that the more rapidly dentine neoformation is initiated, the quicker pulp homeostasis and health are re-established.

It is noted that the conventional treatments for the different stages of pulpitis are directed towards removal of the irritations that cause the inflammation trigger.

Bone defects often result from tumor resection, congenital malformation, trauma, fractures, surgery, or periodontitis in dentistry and periapical lesions due chronic pulpitis. The edentulism of the jaws and the periodontal disease represent conditions that frequently lead to disruption of the alveolar bone. The loss of the tooth and its bone support, lead to the creation of dental jaw defects or situation of maxillary atrophy. The restoration of a functional condition involves the use of endosseous implant which requires adequate bone volume, to manage the masticatory load. Several techniques combine these principles with different results, due to the condition of the bone base, the surgical technique that is used, and the bone metabolic conditions of the patient that can be in a state of systemic osteopenia or osteoporosis; these can also affect the result of jaw bone reconstruction.

Thus, although dental implants serve as an effective treatment to recover mouth function from tooth defects, many patients do not have the adequate bone volume for an – implant. The currently used gold standard for the reconstruction of large bone defects is the use of autogenous bone grafts. While autogenous bone graft is the most effective clinical method of osseous defects, surgical stress to the part of the bone being extracted and the quantity of extractable bone limit this method.

The present invention provides a new approach for dental pulp and/or dental jaw bone therapy, in which *Cannabis* extract and/or derivatives thereof (e.g. THC, CBD) or at least one synthetic cannabinoid are used and found effective for treating the inflammation process itself. pain related with dental pulp inflammation and contribute to bone regeneration. Without being bound by theory, some compositions of the present invention may be efficacious in stimulation of osteoprogenitor cells to differentiate into osteoblasts and begin formation of new bone.

It is within the scope that the composition of the present invention is effective in induction and promotion of biological processes associated with bone regeneration such as osteogenesis, osteoinduction and osteoconduction.

According to one embodiment of the present invention, a cannabinoid-based composition useful for treating or preventing dental pulp associated diseases is disclosed. In a main aspect, said composition comprises an effective amount of *Cannabis* extract or a derivative thereof or at least one synthetic cannabinoid for the treatment of dental pulp inflammation conditions and various bone defects.

According to a further embodiment of the present invention, the composition as defined in any of the above comprises a predefined ratio of Tetrahydrocannabinol (THC) or a derivative thereof: CBD or a derivative thereof effective for said treatment of dental pulp inflammation conditions and dental alveolar bone defects.

According to a further embodiment of the present invention, the dental pulp inflammation conditions and bone defects are selected from the group consisting of: dentine damage, pulpal inflammation, pulpitis, reversible pulpitis, irreversible pulpitis, acute pulpitis, chronic pulpitis, pulp necrosis, infection, periodontitis, apical peridontitis, apical abscess, bifurcation bone defects, pain and any combination thereof.

According to a further embodiment of the present invention, the composition is formulated for application mode selected from the group consisting of: coronal, intra pulpa, apical, periapical, intra canal, intra bone, intra apical foramen and any combination thereof.

As used herein, the term "*Cannabis*" refers hereinafter to a genus of flowering plants that includes, amongst others three different species, *Cannabis sativa, Cannabis indica* and *Cannabis ruderalis.*

The term "*Cannabis* extract or a derivative thereof" refers hereinafter to *Cannabis* extract or *Cannabis* concentrates or fractions or compounds (including isolated compounds) thereof that are used as components of the composition of the present invention. Such an extract or a derivative thereof may include cannabinoid-type compounds or fractions, non-cannabinoid-type compounds or fractions and combinations thereof. It further refers to any extract or concentrate derived from the *Cannabis* plant which contains at least one cannabinoid. The cannabinoids may be extracted from the *Cannabis* plant using any one of the many known extraction methods, such as non-hydrocarbons extraction methods and hydrocarbons extraction methods. It is also within the scope that the *Cannabis* extract may be treated by separation or purification or fractionation processes. It further refers to purified or partially purified *Cannabis* extract containing cannabinoid-type portions or elements. In alternative embodiments, cannabinoid extract or derivative thereof may contain synthetic cannabinoids.

The term "Cannabinoid" refer hereinafter to a class of diverse chemical compounds that act on cannabinoid receptors and other signal transduction receptors or proteins on cells that repress or activate neurotransmitter release in the brain, heart, liver, immune system and lungs. These receptor proteins include the endocannabinoids (produced naturally in the body by humans and animals), the phytocannabinoids (found in *Cannabis* and some other plants), and synthetic cannabinoids (manufactured chemically). The most notable cannabinoid is the phytocannabinoid Δ9-tetrahydrocannabinol (THC), the primary psychoactive compound of *cannabis*. Cannabidiol (CBD) is another major constituent of the plant, representing up to 40% in extracts of the plant resin. There are at least 85 different cannabinoids isolated from *cannabis*, exhibiting varied effects. Reference is now made to www.medicinalgenomics.com/wp-content/uploads/2011/12/Chemical-constituents-of-cannabis.pdf, which is incorporated herein by reference in its entirety, presenting a non-limiting list of identified cannabinoids. The current invention includes within its scope all cannabinoids, for example, cannabinoids belonging to the following classes or groups:

Cannabigerol (CBG) type: including CBG, and its precursor cannabigerolic acid (CBGA) shown to be a biogenic cannabinoid formed in the plant. Propyl side-chain analogs and a monomethyl ether derivative are other cannabinoids of this group.

Cannabichromene (CBC) type: Five CBC-type cannabinoids, mainly present as C5-analogs, have been identified.

Cannabidiol (CBD) type: Seven CBD-type cannabinoids with C1 to C5 side chains have been described. CBD and its corresponding acid CBDA are the most abundant cannabinoids in fiber-type *Cannabis* (industrial hemp). CBDA was the first discovered cannabinoid acid.

Δ9-Tetrahydrocannabinol (THC) type: Nine THC-type cannabinoids with C1 to C5 side chains are known. The major biogenic precursor is the THC acid A, whereas THC acid B is present to a much lesser extent. THC is the main psychotropic principle; the acids are not psychoactive. THC (6a,10a-trans-6a,7,8,10a-tetrahydro-6,6,9-trimethyl-3-pentyl-6H-dibenzo[b,d]pyran-1-ol) are also included within this group.

Δ8-THC type: Δ8-THC and its acid precursor are considered as THC and THC acid artifacts, respectively. The 8,9 double-bond position is thermodynamically more stable than the 9,10 position. Δ8-THC is approximately. 20% less active than THC.

Cannabicyclol (CBL) type: Three cannabinoids characterized by a five-atom ring and C1-bridge instead of the typical ring A are known: CBL, its acid precursor, and the C3 side-chain analog. CBL is known to be a heat-generated artifact from CBC.

Cannabielsoin (CBE) type: Among the five CBE-type cannabinoids, which are artifacts formed from CBD, are CBE and its acid precursors A and B.

Cannabinol (CBN) and Cannabinodiol (CBND) types: Six CBN- and two CBND-type cannabinoids are known. With ring A aromatized, they are oxidation artifacts of THC and CBD, respectively. Their concentration in *Cannabis* products depends on age and storage conditions.

Cannabitriol (CBT) type: Nine CBT-type cannabinoids have been identified, which are characterized by additional OH substitution. CBT itself exists in the form of both isomers and the racemate, whereas two isomers (9-a- and 9-b-hydroxy) of CBTV were identified. CBDA tetrahydrocannabitriol ester (ester at 9-hydroxy group) is the only reported ester of any naturally occurring cannabinoids.

Miscellaneous types: Eleven cannabinoids of various unusual structure, e.g., with a furano ring (dehydrocannabifuran, cannabifuran), carbonyl function (cannabichromanon, 10-oxo-G-6a-tetrahydrocannabinol), or tetrahydroxy substitution (cannabiripsol), are known.

The term "cannabidiol" or "CBD" refers hereinafter is a major phytocannabinoid, accounting for up to 40% of the plant's extract. Cannabidiol has a very low affinity for CB1 and CB2 receptors but acts as an indirect antagonist of their agonists. CBD may potentiate THC's effects by increasing CB1 receptor density or through another CB1-related mechanism. It is also an inverse agonist of CB2 receptors. CBD possesses antiproliferative, pro-apoptotic effects and inhibits cancer cell migration, adhesion and invasion. The term CBD also refers to Cannabidivarin (CBDV) a homolog of cannabidiol (CBD) and to cannabidiolic acid (CBDA).

The term "Tetrahydrocannabidiol" or "THC" refers hereinafter to the principal psychoactive constituent (or cannabinoid) of the Cannabis plant. THC has a partial agonist activity at the cannabinoid receptor CB1 and the CB2 receptor and is known to increase cortisol levels. It is further included within the scope that the term THC further refers to Tetrahydrocannabivarin (THCV or THV) a homologue of tetrahydrocannabinol (THC) and Tetrahydrocannabinolic acid (THCA, 2-COOH-THC), a biosynthetic precursor of tetrahydrocannabinol (THC).

It is noted that cannabinol (CBN), cannabichromene (CBC), the acids (CBDA, CBGA, THCA) and propyl homologues (CBDV, CBGV, THCV) of CBD, cannabigerol (CBG) and THC, and tetrahydrocannabivarin acid (THC-V and THC-VA) are also included as optional active ingredient(s) of the composition or formulation of the present invention.

The Cannabis extract or a fraction thereof may comprise noncannabinoid-type constituents selected from the group consisting of: terpenoids, hydrocarbons, essential oil derived from Cannabis, nitrogen-containing compounds, carbohydrates, flavonoids, fatty acids, noncannabinoid phenols, simple alcohols, aldehydes, ketones, acids, esters, lactones, phytosterols such as campesterol, ergosterol, E-sitosterol, and stigmasterol, vitamin K, pigments such as carotene and xanthophylls, elements such as Na, K, Ca, Mg, Fe, Cu, Mn, Zn and Hg and any combination thereof. Reference is made to the publication of www.medicinalgenomics.com/wp-content/uploads/2011/12/Chemical-constituents-of-cannabis. pdf, which is incorporated herein by reference in its entirety. It is further within the scope that there are 483 different identifiable chemical constituents known to exist in cannabis. The most distinctive and specific class of compounds are the cannabinoids, that are only known to exist in the Cannabis plant. Other constituents of the Cannabis plant are: nitrogenous compounds, amino acids, proteins, glycoproteins, enzymes, sugars and related compounds, hydrocarbons, simple alcohols, aldehydes, ketones, simple acids, fatty acids, simple esters, lactones, steroids, terpenes, non-cannabinoid phenols, flavonoids, vitamins [Vitamin A], pigments, and elements. It is further within the scope that medicalmarijuana.procon.org/view.answers.php?questionID=000636 is incorporated herein in its entirety.

The term "cannabinoid receptor" refers hereinafter to a class of cell membrane receptors under the G protein-coupled receptor superfamily. There are currently two known subtypes of cannabinoid receptors, termed CB1 and CB2. The CB1 receptor is expressed mainly in the brain, but also in the lungs, liver and kidneys. The CB2 receptor is expressed mainly in the immune system, the digestive system and in hematopoietic cells.

The term "synthetic cannabinoid" generally refers to synthesized compounds that are related to chemicals found in the marijuana plant. They may be sprayed on dried, shredded plant material so they can be smoked (herbal incense) or sold as liquids to be vaporized and inhaled in e-cigarettes and other devices (liquid incense). It is further acknowledged that synthetic cannabinoids are a class of compounds that are different from the cannabinoids found in Cannabis but which also bind to cannabinoid receptors. For example, there are several psychoactive artificial cannabinoid families (e.g. AM-xxx, HU-xxx, JWH-xxx, CP xx) that are sprayed onto plant matter that is then sold under brand names like K2 and Spice both of which are often used as generic terms used for any synthetic cannabinoid product. Many synthetic cannabinoids act on the body in a similar way to cannabinoids naturally found in Cannabis, such as THC or CBD.

Non limiting examples of synthetic cannabinoids within the scope of the present invention include: 4-HTMPIPO, 5F-AB-FUPPYCA, 5F-AB-PINACA, 5F-ADB, 5F-AD-BICA, 5F-ADB-PINACA, 5F-AMB, 5F-AMB-PICA, 5F-APINACA, 5F-CUMYL-PINACA, 5F-EMB-PINACA, 5F-NNE1, 5F-PB-22, 5F-PCN, 5F-SDB-006, A-836339, AB-001, AB-005, AB-CHFUPYCA, AB-CHMINACA, AB-FUBICA, AB-FUBINACA, AB-PICA, AB-PINACA, ADB-CHMINACA, ADB-FUBICA, ADB-FUBINACA, ADB-PINACA, ADBICA, ADAMANTYL-THPINACA, ADBICA, ADSB-FUB-187, AM251, AM-404, AM-630, AM-678 (=JWH-018), AM-679, AM-694, AM-1220, AM-1221, AM-1235, AM-1241, AM-1248, AM-2201, AM-2232, AM-2233, AM-2389, AMB-CHMINACA, AMB-FUBINACA, APICA, APINACA, APP-FUBINACA, BAY 38-7271, BAY 59-3074, BB-22, BIM-018, BML-190, BRL-4664, Cannabicyclohexanol, CB-13, CP-47497, CP-55940, CP-55244, CT-3, CUMYL-PICA, CUMYL-PINACA, CUMYL-THPINACA, DMA (5'-dimethylammonium delta-8-tetrahydrocannabinol), TMA (5'-trimethylammonium delta-8-tetrahydrocannabinol) (water-soluble), DMHP, EAM-2201, FAB-144, FDU-NNE1, FDU-PB-22, FUB-144, FUB-APINACA, FUB-JWH-018, FUB-PB-22, FUBIMINA, GW-405,833, HHC, HU-210, HU-211, HU-239, HU-243, HU-308, JWH-007, JWH-015, JWH-018, JWH-019, JWH-073, JWH-081, JWH-098, JWH-116, JWH-122, JWH-133, JWH-149, JWH-167, JWH-182, JWH-193, JWH-198, JWH-200, JWH-203, JWH-210, JWH-249, JWH-250, JWH-251, JWH-302, JWH-398, JWH-424, JTE-907, JTE 7-31, L-759,633, L-759,656, LY-2183240, LY-320135, MAM-2201, MDA-19, MDMB-CHMICA, MDMB-CHMINACA, MDMB-FUBICA, MDMB-FUBINACA, MEPIRAPIM, MN-18, MN-25, Nantradol, Nabilone, Nabitan, NESS-0327, NESS-04005, NM-2201, NNE1, O-774, O-1057, O-1812, O-2050, O-2694, O-6629, Org 28611, PB-22, PF-03550096, PTI-1, PTI-2, PX-1, PX-2, PX-3, RCS-4, RCS-8, SDB-005, SDB-006, SP-111, SR-141716A, SR-144528, STS-135, Synhexyl, THJ-018, THJ-2201, UR-144, WIN-48098, WIN-54461, WIN-55212-2, WIN-55225, WIN-56098, XLR-11, abn-CBD, O-2654 and any combination thereof.

Figure 1:
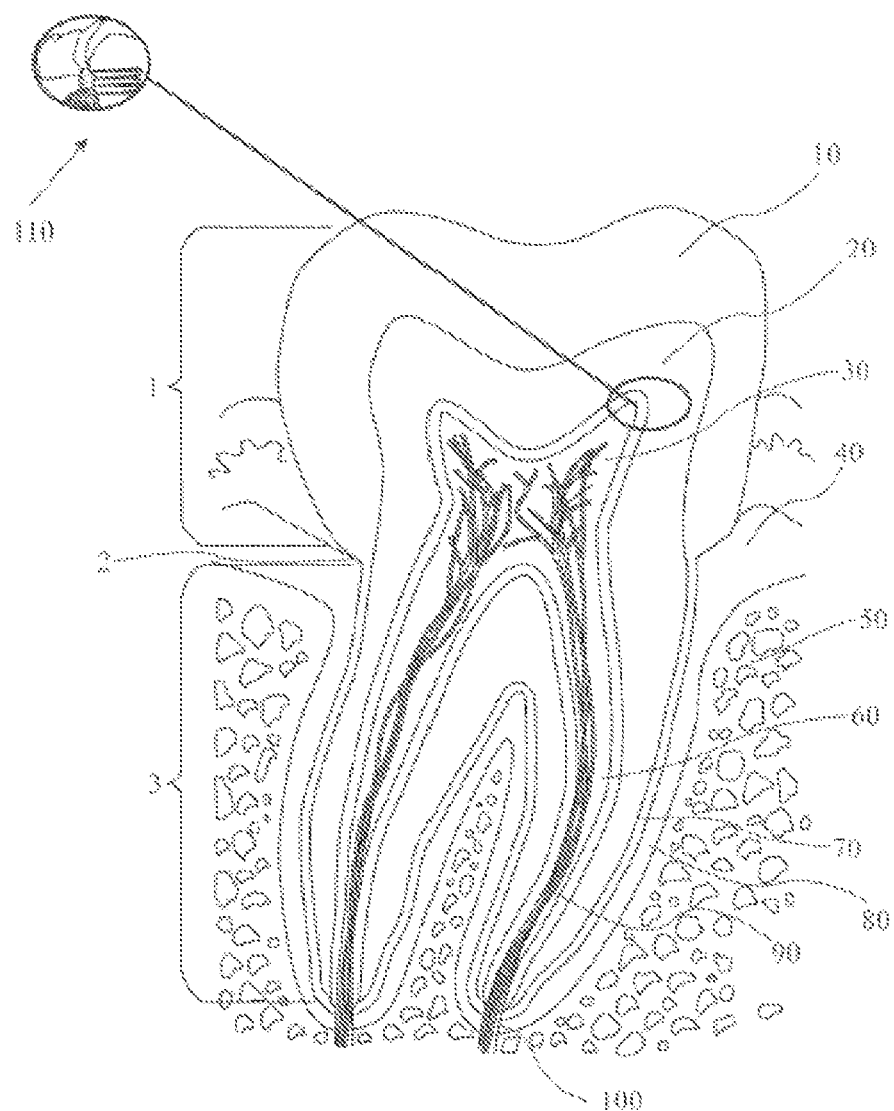

Reference is now made to FIG. 1 schematically presenting dental pulp anatomy, inter alia comprising:

Crown (1): The visible part of the tooth. It is normally covered by enamel.

Neck (2): The area where the crown joins the root. In other words, constricted area between the crown and the root of the tooth Root (3): Part of the tooth inside the bone socket.

Enamel (10): Hard calcified tissue covering the dentin of the crown of tooth. Because it contains no living cells, tooth enamel cannot repair damage from decay or from wear, it can only be done by a dentist. Enamel prism, is a tightly packed mass of hydroxyapatite crystals in an organized pattern.

Dentin (20): That part of the tooth that is beneath enamel and cementum. It contains microscopic tubules (small hollow tubes or prisms). Dentin loses its protective covering (enamel), the tubules allow heat and cold or acidic or sticky foods to stimulate the nerves and cells inside the tooth, causing sensitivity.

Pulp Chamber (30): The space at the center of the teeth containing nerves, blood vessels and connective tissue.

Gums (also called gingiva) (40): Soft tissues that cover and protect the roots of the teeth and cover teeth that have not yet erupted.

Bone (50): Bone that supports the tooth, or in other words, the part of the jaw that surrounds the roots of the teeth.

Root Canal (60): The portion of the pulp cavity inside the root of a tooth; the chamber within the root of the tooth that contains the pulp. The passageway for nerves and blood vessels.

Cementum (70): Hard connective tissue covering the tooth root, giving attachment to the periodontal ligament.

Periodontal Ligament (80): A system of collagenous connective tissue fibers that connect the root of a tooth to its socket. Fibrous tissue that separates the tooth from the bone socket and anchors the tooth to the bone.

Nerves and blood vessels (90): Supply the tooth with nutrients.

Plexus of Raschkow (100): Located central to the cell-rich zone. The plexus of Raschkow monitors painful sensations. By virtue of their peptide content, the nerve plexus of Raschkow also play important functions in inflammatory events and subsequent tissue repair.

An enlarged view of the interface between the pulp (30) and the dentin (20) is shown in (110).

The term "pulp" or "dental pulp" refers hereinafter to the part in the center of a tooth made up of living connective tissue and cells called odontoblasts. The dental pulp is a part of the denting pulp complex (endodontium). The vitality of the dentin-pulp complex, both during health and after injury, depends on pulp cell activity and the signaling processes that regulate the cell's behavior. According to further aspects, the pulp is the neurovascular bundle central to each tooth, permanent or primary. It comprises a central pulp chamber, pulp horns and radicular canals. The large mass of pulp is contained within the pulp chamber, which is contained in and mimics the overall shape of the crown of the tooth. It is noted that because of the continuous deposition of dentin, the pulp chamber size is decreased with age. Radicular pulp canals extend down from the cervical region of the crown to the root apex. They are continues with the periapical tissues through the apical foramen or foramina. Accessory canals are pathways from the radicular pulp, extending laterally through the dentin to the periodontal tissue seen especially in the apical third of the root. Accessory canals are also called lateral canals, because they are usually located on the lateral surface of the roots of the teeth. To summarize, pulp characteristics and properties include:

Formative organ of the tooth.
Builds primary dentine during the development of the tooth.
Builds secondary dentin after tooth eruption.
Responsible for formation of reparative dentin in response to stimulation, as long as odontoblast remain vital.

As used herein, the term "odontoblast" refers hereinafter to a cell of neural crest origin that is part of the outer surface of the dental pulp, and whose biological function is dentinogenesis, which is the formation of dentin, the substance beneath the tooth enamel on the crown and the cementum on the root.

The term "pulpitis" as used herein refers hereinafter to inflammation of dental pulp tissue. The pulp contains the blood vessels, the nerves and connective tissue inside a tooth, and provides the tooth's blood and nutrients. Pulpitis is mainly caused by bacteria infection which itself is a secondary development of caries (tooth decay). It manifests itself in the form of a toothache.

The term "reversible pulpitis" is herein defines as a mild inflammation of the dental pulp. It can be caused by irritation of the pulp. Some common causes of reversible pulpitis may include:

cavities that have not reached the nerve yet, erosion of the tooth that reaches the dentin, drilling done by a dentist when doing a filling or crown preparation on the a fracture of the enamel layer of the tooth which can expose the dentin It is further acknowledged that the symptoms of reversible pulpitis can range from absence of symptoms to a sharp pain when they are stimulated by stimuli such as cold.

Reversible pulpitis is indeed reversible; it can be alleviated by removing the cause of the disease. Thus reversible pulpitis can be cured by finding the cause of the inflammation, and remove it.

The term "irreversible pulpitis" refers to a severe inflammation of the dental pulp. Irreversible pulpitis often occurs after reversible pulpitis when the severity of the irritants is high or pulp exposed for prolonged time that causes irreversible pulpitis and further by the following non-limiting examples:

Removal of large amounts of enamel and dentin due to deep caries lesions, same on preparations of elements for crowns and bridges, and gets close to the pulp.

When the blood flow supply to the pulp is decreased or removed (this can be caused by orthodontic treatment).

It could also be caused by trauma.

All above examples are, causing irritation and activating an inflammatory response. Due that response an hyperemia occurs in the pulp, with obliterations of the nerve bundle, and necrosis of the dental pulp.

It is within the scope of the present invention that the symptoms of irreversible pulpitis can range from no symptoms at all to an excruciating spontaneous pain. The tooth can be very sensitive even to a small temperature change, such as breathing in room-temperature air. The pain usually remains even after the cause or symptom is removed.

Up-to-the provision of the composition and method of the present invention, there was no cure for irreversible pulpitis. The only known way to treat irreversible pulpitis is to have a root canal treatment performed. The term "acute pulpitis" refers hereinafter to inflammatory process in the pulp which is characterized by spontaneous pain, radiating pain, can intensify at night. Acute dental pain most often occurs in relation to inflammatory conditions in the dental pulp or in the periapical tissues surrounding a tooth.

Up until the present invention, there were two main ways to treat pulpitis: conservative way and surgical.

Reference is now made to the conservative method of treatment of reversible pulpitis, which mainly consists of the following stages: anesthesia; removal of necrotic dentin; placement of a base layer and filling with composite material.

Reference is now made to operative (surgical) way of treatment of irreversible pulpitis. This method consists in removal (amputation) of pulp from the root canal system, rinsing and filling with special material gutta-percha and sealers.

In surgical treatment, in the 1st treatment, the tooth is anaesthetized and the pulp tissue is removed, material or paste such as Calcium hydroxide ($CaOH_2$, Ledermix) is placed in the root canals (for between 24 hr and 15 days) the element is closed with PTFE, Cavit G temporary filling and on top an galssionomer as Fuji IX filling.

The term "chronic pulpitis" refers hereinafter to a form of pulpitis which is the result of latent long time exposure to irritants and combines periapical signs, painful on percussion due to periapical lesions.

It is acknowledged in this respect that inflammation of pulp is often a consequence of physical, mechanical and chemical injuries.

It is herein noted that transition of the disease into a chronic form may be a consequence of the untreated acute stage of pulpitis. The patient may feel that the inflammatory process has passed, but, in fact, the disease will continue to progress in periapical region.

Reference is now made to the symptoms of chronic pulpitis. It is noted that pain resulted from chronic pulpitis is more tolerable than with acute pulpitis. It is aching and rarely radiates along the trigeminal nerve trunks.

Symptoms of chronic pulpitis are varied and depend on its type.

With respect to treatment of chronic pulpitis, it is within the scope that the provision of the therapeutic compositions of the present invention addresses the major aspects needed for treatment of pulpitis:

Elimination of pain symptoms through the elimination of an inflammatory focus in the pulp
Reduction of the inter radicular canal pressure
Promotion of healing and dentin formation
Prevention of the development of apical periodontitis
Prevention of the development of periodontitis As used herein, the term "necrotic pulp" refers hereinafter to dental pulp within a tooth which has become necrotic. In other words, it refers to non vital pulp tissue. This means that the tooth pulp doesn't have blood supply. When this happens, the hollow root canal and pulp chamber inside the tooth become a potential site of bacterial colonization, can spread through the apical foramina. This may be painful and may cause severe toothache in the affected person. Sequelae of a necrotic pulp include acute apical periodontitis, radicular cyst with formation of fistula that communicates true an opening to the attached gingiva on the labial or lingual side of the alveolar process. Often this is accompanied by pain, swelling, and inability to chew on the affected tooth. Sometimes numbness can occur, due to the pressure the infectious fluid places on nearby nerves in the alveolar bone.

It is further acknowledged in this respect that usually, necrotic pulps are the end results of the process of pulp tissue degeneration.

The conventional treatment of necrotic pulp usually involves endodontic treatment.

Conditions causing necrotic pulp include: traumatic injury, extensive tooth decay, rapid orthodontic tooth movement, periodontal disease and chronic pulpitis.

It is emphasized that treatment of pulp inflammation, should include relieve of the pain, elimination of the infection and, morphologic restoration of the tooth.

Reference is now made to "dental bone defects", which herein refer to bone or osseous or alveolar bone defects including concavities or deformities in the alveolar bone involving one or more teeth. It is acknowledged that procedures designed to modify and re-shape defects and deformities in the bone surrounding the teeth are called osseous surgery. The most common pattern of bone loss is reduction in height of bone, 2-3 wall defects due periodontal diseases.

The term "furcation involvement" refers hereinafter to a condition in which bifurcation and trifurcations of multi-rooted teeth (the areas where the tooth root splits) are invaded by bacteria's named periodontal disease process.

The objectives of treatment of these dental bone defects by the composition of the present invention include: elimination of the periodontal lesion, achievement of a tissue that will allow efficient plaque control, bone formation and new attachment and improved tooth support.

It is further within the scope of the present invention that bone defects and furcation involvement is a consequence of untreated periodontitis. Dental plaque is the major cause of periodontitis. Persistent infection of the gum margins leads to progressive inflammation and destruction of the supporting tissues by bacterial toxins. Extension and the hardening of plaque lead to formation of tartar beneath the gums. Having tartar within the gum pockets can lead to periodontitis. It can form a reservoir of bacteria which maintains inflammation and prevents healing, destroying the Periodontal ligament round the tooth causing to loss of bone attachment and finally loss of the teeth affected.

Reference is now made to examples of classifications of bone defects within the scope of the current invention:

One wall defect—usually only one interdental wall remains and is called hemi septum if remaining wall is proximal. Poor prognosis for the currently conventionally used periodontal regeneration since it is difficult to stabilize the graft material that is used in its proper place.

Two wall defect—most prevalent bone defect found interdentally with facial and lingual walls remaining, involves both the interproximal walls which are mainly called crater defects or interdental crater defects.

Three wall defect—occurs most frequently in the interdental region, usually the remaining bony walls are facial, lingual and proximal can be circumferential defects. Only this defect enables the stabilization of a graft material to be used.

Combined defect—combination of one, two or three wall defects.

Fenestration—isolated areas in which the root is denuded of bone and the root surface is covered only by periosteum and overlying gums. Marginal bone is intact.

Dehiscence—areas where the defect extends through the marginal bone.

Reference is now made to examples of classification of "furcation involvements" within the scope of the present invention:

Grade I involvement—also known as incipient or early lesion, there is slight bone loss in the furcation area and usually no x-ray or radiographic findings are present.

Grade II involvement—bone destruction is present and there is partial penetration of probe into furcation area. The lesion is also known as cul-de-sac (A passage with access only at one end) and x-ray or radiograph may or may not show changes.

Grade III involvement—interradicular bone (the bone between the roots of tooth) is completely lost but the defect is covered by gums therefore the furcation is not visible clinically. There is a radiolucent area seen between the roots in lower molars in the x-ray or radiograph.

Grade IV involvement—interradicular bone is completely destroyed, gums are receded and the furcation of tooth is clinically visible.

The objectives of treatment of these furcation defects by the composition of the present invention include: induction of regeneration of the new bone, osseous repair and guided tissue regeneration (GTR).

The present invention provides novel cannabinoid-based compositions and methods which treat inflammation and pain related to dental pulp and are effective in:
- Maintaining odontoblast vitality, i.e. by application of cannabinoid composition to the coronal part of the tooth.
- Treatment of reversible pulpitis, i.e. by application of cannabinoid composition to the coronal or dentin part of the tooth.
- Treatment of irreversible pulpitis i.e. by intrapulpal application of cannabinoid composition.
- Treatment of acute, chronic and necrotic pulpitis, by intracanal application of cannabinoid composition and adjacent the apical foramina.
- Treatment and/or prevention of apical periodontitis by injection or application of cannabinoid composition intrabone.
- Treatment of dental bone defects and/or implant integration stimulation by intrabone application into the defected site and or implantation bone site.

It is well within the scope of the present invention to provide cannabinoid compositions specifically formulated for treatment of each of the above conditions; by applying different THC: CBD ratio and by different types of delivery adapted for different target tissue or organ.

According to further embodiments, the cannabinoid compositions of the present invention have advantageous properties of building the bone, reducing the intrapulpar canal pressure, reversing or treating irreversible pulpitis and improving implant therapy success.

It is submitted that the common and available methods, compositions and treatments are directed towards induction of secondary dentin production by odontoblasts cells. The produced secondary dentin provides protective covering for the dental tubules opening and reduces the hydrodynamic effect which triggers dental hypersensitivity. The commonly available methods and compositions do not treat the inflammation process within the dental pulp that cause intracanal high pressure and therefore do not prevent the pulp and nerves obliteration process due the high intracanal pressure. On the other hand, the present invention is directed to targeted therapy that locally reduces the inflammation of the pulp at different stages of the disease (inflammatory, infectious and necrotic levels). By the provision of cannabinoid based compositions, applied directly to the root canal, reduction of pulp inflammation and prevention of obliteration of the nerves in the root canal is achieved, therefore the vitality of the dental nerves is maintained. It is emphasized that none of the currently available materials used in dentistry are effective in reducing and treating inflammation within the dental root canal by intrapulpal application.

Figure 2:
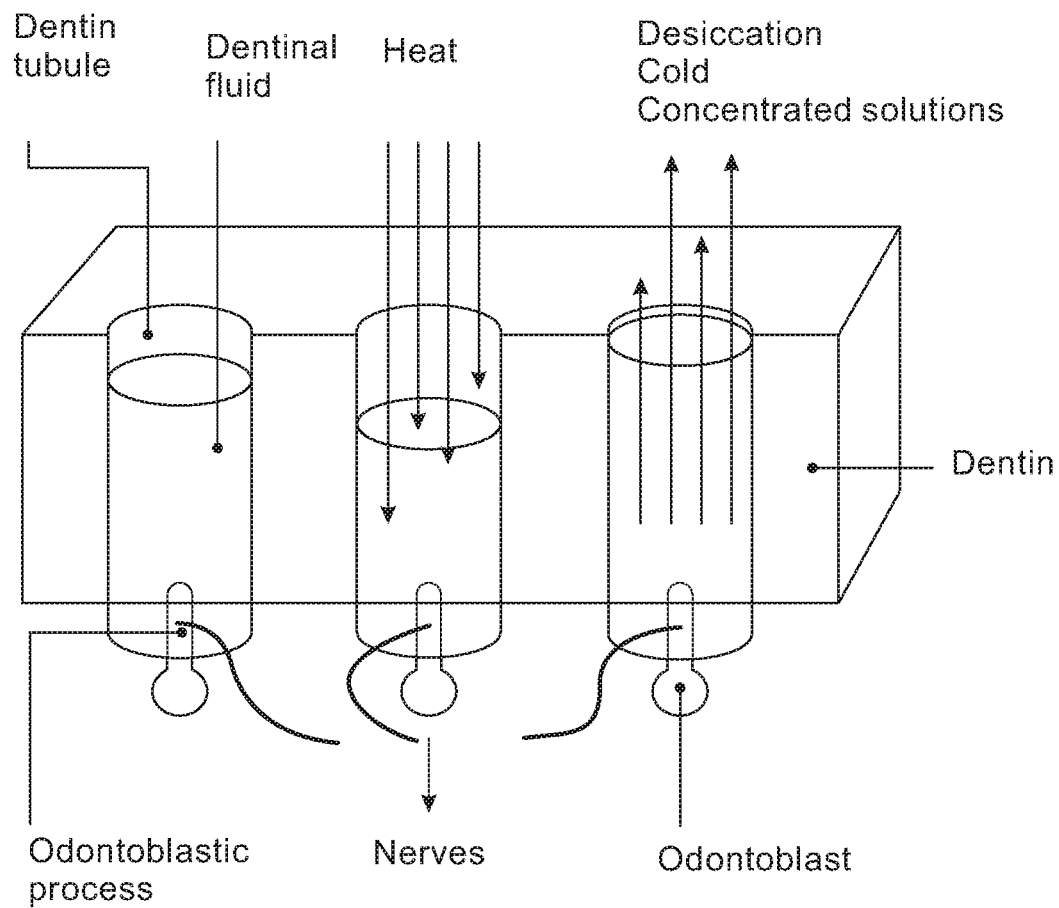

Reference is now made to FIG. 2 schematically illustrating the Brännström's hydrodynamic theory. It is herein acknowledged that the hydrodynamic theory is a theory in dentistry, which describes the mechanism by which a tooth perceives sensation. It states that the flow of fluid in dentinal tubules triggers receptors within the tooth. The aforementioned theory suggests that dentine hypersensitivity is due to movement of fluid within the dentinal tubules in response to mechanical, osmotic, and thermic stimuli. Cold stimuli cause an outward flow of fluid and hot stimuli cause an inward flow. Without wishing to be bound by theory, studies have shown that the main cause of dentinal pain is a rapid outward flow of fluid in the dentinal tubules that is initiated by strong capillary forces.

According to further aspects of the invention, the main causes of pulpal inflammation and changes in dental nervous perception include at least one of:
- Bacterial toxins stimulus, i.e. caries
- Chemical stimulus
- Thermal stimulus
- Mechanic stimulus Reference is now made to FIG. 3, schematically describing a flowchart of pulpal inflammation process, according to certain embodiments of the present invention. In this fig., stimuli (i.e. bacterial, chemical, thermal, mechanical) cause pulpar canal changes and disorders which increase the intra canal pressure. The higher intra canal pressure cause nervous plexus obliteration which results in pulp death, leading to necrosis and periapical lesions.

Figure 4:
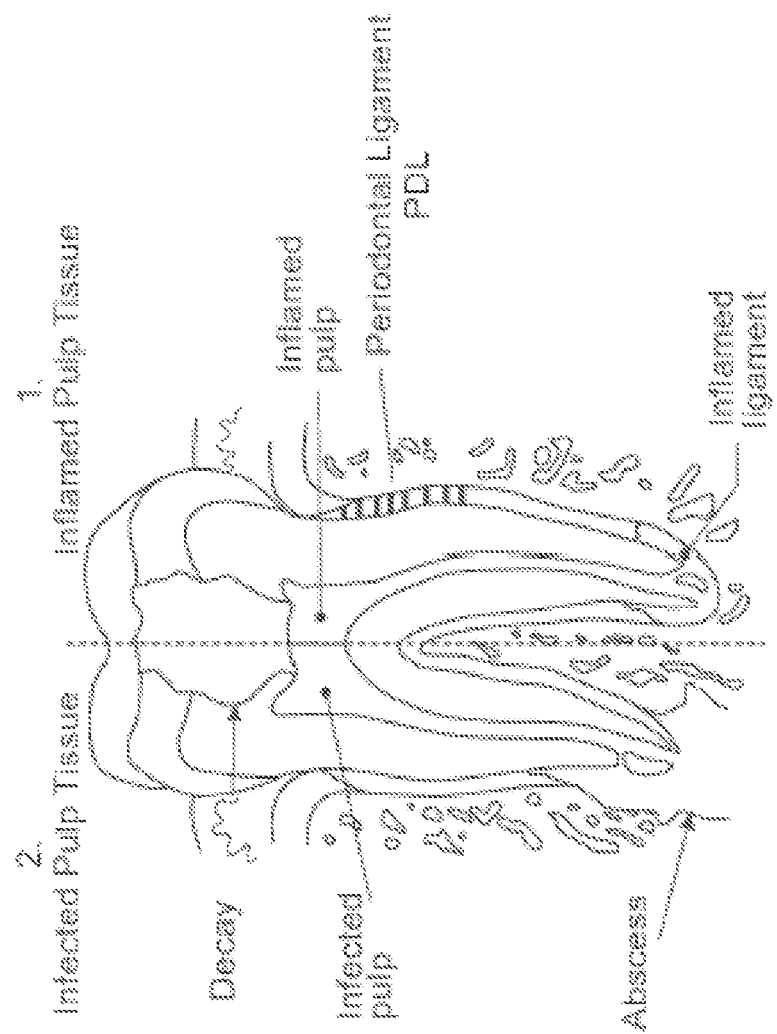

Reference is now made to FIG. 4 schematically illustrating dental pulp pathology. The tooth pulp (or dental pulp) is a soft tissue that maintains blood flow and comprises nerves that surrounds the root. Therefore it can be vulnerable to infection if the first two protective layers, the enamel and dentin, are compromised by a cavity, crack in the tooth or trauma (a decay shown in FIG. 4). The right part (1) of FIG. 4 shows inflammation of the tooth's pulp, which is called pulpitis. It is within the scope that inflammation of the pulp can lead to infection and a possible abscess in the tooth, shown in the left part (2) of FIG. 4. It is noted that if the pulp is infected by bacteria, the area can become inflamed. Untreated inflammation can cause infection which can subsequently devitalize the dental pulp.

According to further aspects, an abscess is an infection in or around the root of the tooth which may or may not be painful. It occurs when the pulp, which is the soft tissue inside the root canal, dies and becomes inflamed and not treated. The most common symptom of an abscess is an ache in the bone around the tooth, but pain when chewing, swelling of the gums, or other symptoms may also be experienced. A dental abscess is usually treated with root canal treatment or endodontic surgery. In this common treatment, an endodontist removes the bacteria from the canals within the tooth, clean, shape and fill the root canals, and seals the space. A crown or other restoration is placed on the tooth to protect and restore it to functionality.

Figure 5:
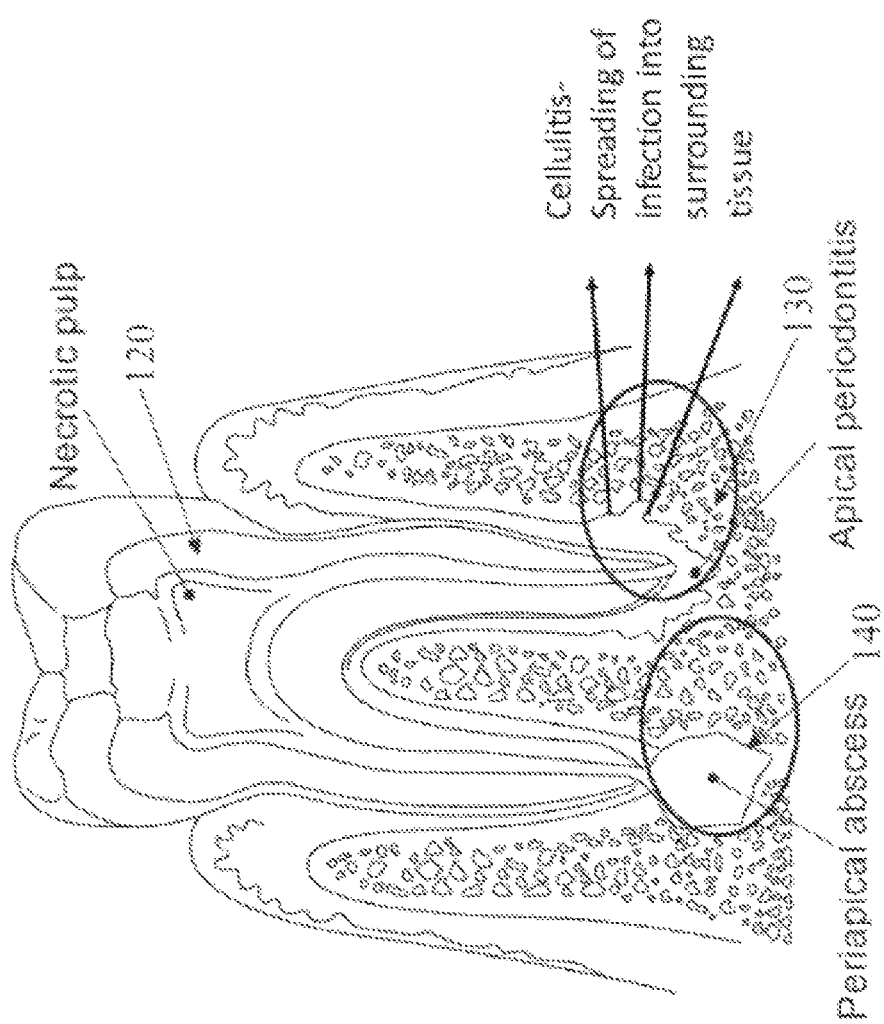

Reference is now made to FIG. 5 schematically illustrating acute pulpitis, chronic pulpitis and necrosis features. In these embodiments, tooth decay, cracks, trauma and repeated dental procedures can lead to irreversible inflammation of the pulp. Not treated pulp in this condition leads to necrosis. The necrotic pulp tissue (120) will then cause infection (i.e. apical periodontitis, inflammation of all the supporting structures of the teeth in the area surrounding the apex of the tooth) (130) or periapical abscess (140) in the bone surrounding the root. Without treatment, the infection can spread into tissue spaces of the head and neck, becoming cellulitis (i.e. spreading of the infection into surrounding tissues).

The present invention provides an alternative and advantagous treatment for all stages of dental pulp disease which avoids the undesirable, painful, inconvenient and unpleasant procedures of root canal treatment and/or endodontic surgery and simultaneously maintains the diseased tooth viable and functional.

In one embodiment, the present invention provides cannabinoid based compositions applied directly to the target site, specifically adapted to treat dental pulp inflammation, infection and necrosis. The aforementioned compositions can be applied at the coronal or topical part of the tooth to maintain odontoblasts viability and dentin production, injected intra pulpar to treat dental pulp inflammation (reversible pulpitis) or by apical or intra bone application to treat dental pulp infection or necrosis, apical periodontitis.

Thus the present invention provides novel and efficacious treatment for pulp disease in its inflammatory, infectious and necrotic levels.

Reference is now made to the publication of Cannabinoid receptor 1 (CB1R) expression in rat dental pulp Somsak Mitrirattanakul, Sopee Poomsawat, Pornpoj FuangtharnthipOral Science International Volume 9, Issue 1, Pages 17-20 (May 2012) DOI: 10.1016/S1348-8643(12)00003-1Copyright © 2012 Japanese Stomatological Society Terms and Conditions, incorporated herein by reference. In this publication, the expression of Cannabinoid receptor 1 (CB1R) in rat dental pulp was examined by immunohistochemistry. It was reported that CB1R immunoreactivity was found on nerve fibers in radicular pulp and in the subodontoblastic layer.

The present invention provides for the first time a treatment for dental pulp diseases and conditions which is based on cannabinoids, specifically THC and CBD, applied in different ratios, directly to the dental pulp.

According to one aspect of the present invention, the present invention provides an anti-inflammatory *Cannabis* composition comprising a predefined CBD/THC ratio which maintains odontoblast cells vitality. According to a further embodiment, the cannabinoid based composition of the present invention provides an anti-inflammatory and antinociceptive effect in various painful dental conditions. This effect can be mediated through the nociceptive afferent nerve terminals.

According to further aspects, the present provides treatment of the following dental-related pathologies and conditions:

Dentin Recovery and Neoformation:
Pulp characteristics include:
Formative organ of the tooth.
Builds primary dentine during the development of the tooth.
Builds secondary dentin after tooth eruption.
Responsible for formation of reparative dentin in response to stimulation, as long as odontoblast remain vital.

The present invention provides a cannabinoid-based composition comprising a predefined
CBD/THC ratio which maintains odontoblast vitality and induces dentine neoformation and recovery.

Pulpitis (See FIG. 4)
The most common cause of dental pain.
The cause of loss of teeth in young persons.
The usual cause of pulpitis is caries penetrating the dentin.
The present invention provides an anti-inflammatory *Cannabis* composition comprising a predefined CBD/THC ratio which destroys or prevents dental caries Pulpal Inflammation:
Pulpal inflammation can be induced by
Mechanical cause
Thermal cause
Chemical cause
Bacterial cause
The present invention provides an anti-inflammatory *Cannabis* composition comprising a predefined CBD/THC ratio which treats and/or prevents dental pulp inflammation, regardless of the cause of the inflammation.

Irreversible Pulpitis:
Persistent inflammatory condition of pulp.
May be symptomatic or asymptomatic
Caused by noxious stimulus.
The present invention provides an anti-inflammatory *Cannabis* composition comprising a predefined CBD/THC ratio which treats and/or prevents irreversible pulpitis and in fact turns it into a reversible condition or disease. The treatment is performed by intrapulpar injection and or direct or topical application of the cannabinoid composition of the present invention.

According to further aspects, the clinical features of irreversible pulpitis at early stage include:
Pain, often continues, after the cause has been removed
The pain is spontaneous.
It is therefore well within the scope that the compositions of the present invention treat and/or prevent the clinically differentiated conditions which characterize reversible pulpitis and irreversible pulpitis.

Reversible pulpitis is a type of inflammation of the pupal tissue, which is symptomatic. The initial stage gives hypersensitive response to any cold stimulus. The pain response subsides when the stimulus is removed. Thus, in reversible pulpitis, pain is generally traceable to a stimulus such as cold water or air.

It is within the scope of the present invention to treat reversible pulpitis by the application of an anti-inflammatory cannabinoid composition, at the dental level.

Acute pulpitis (See FIG. 5):
The clinical features include:
Increased pressure inflammatory exudate.
Rapid spread of inflammation through the pulp associated with pain and necrosis.
It is within the scope of the present invention to treat acute pulpitis by intrapulpal application and/or direct or topical application of an anti-inflammatory cannabinoid composition.

Chronic Pulpitis (See FIG. 5):
May be developed with or without episodes of acute pulpitis.
Many pulps under large carious cavities die painlessly.
First indication is development of periapical periodontitis, either with pain or seen by chance in radiograph.
It is within the scope of the present invention to treat chronic pulpitis by intrapulpar application and/or direct or topical application of an anti-inflammatory cannabinoid composition. In combination with intrabone application or by apical foramen application of an anti-inflammatory cannabinoid composition.

Pulp Necrosis (See FIG. 5):
Causes of necrosis include:
Sequel of inflammation.
Can occur following trauma
It is herein acknowledged that the pulp may be destroyed before an inflammatory reaction.
It is within the scope of the present invention to treat pulp necrosis by intrabone application or by apical foramen application of an anti-inflammatory cannabinoid composition.

The composition of the present invention, comprising THC/CBD is shown to have anti-inflammatory effect, increased bone formation effect and anti-analgesic effect.

Based on the herein disclosed findings, the THC/CBD composition of the present invention is shown to have an effect on the dental human pulp with great importance of its medical use for treatment of about 70% of the human dental system pathologies.

According to main aspects of the present invention, the provision of the following products for treating dental pulp inflammation and dental bone defects and related conditions is disclosed:
1. Anti-inflammatory compositions directed to the coronal part of the tooth.
2. Anti-inflammatory compositions directed to the intrapulpal or canal parts of the tooth.
3. Anti-inflammatory compositions directed to the bone part of the tooth.
4. Anti-inflammatory compositions directed to the alveolar bone.

According to further aspects of the present invention, different types or modes of application of the anti-inflammatory compositions are provided, for example, external application (e.g. tooth neck or cervical region of coronal region) or internal application (e.g. intrapulpal injection or intrabone injection or apical injection or intrabone application).

It is further within the scope that the cannabinoid anti-inflammatory compositions of the present invention may contain, or may be combined with conventional dental materials or ingredients used for pulp diseases or conditions. A synergistic effect with respect to treatment of the dental inflammation-related disease may be obtained between the composition of the present invention and the conventionally used dentistry material. Examples of conventional materials used in dentistry according to different pulp disease phases:

Phase 1—First Stimulus of the Dental Nerve

Reference is now made to external or topical application of the anti-inflammatory composition, mainly on the "tooth neck" or cervical or coronal region. In this aspect, the composition of the present invention may contain materials adapted to seal dental tubules. Non limiting examples of dental materials within the scope of the present invention, useful for external application include:
1. Glutaraldehyde (e.g. in a gel form) treats dentinal hypersensitivity by precipitating plasma proteins, resulting in decreased permeability and inhibited fluid flow into the dentinal tubules. It may be used for the treatment of hypersensitive dentin in cervical areas and in teeth prepared for direct or indirect restorations. For example, GLUMA® Desensitizer PowerGel, KULZER
2. Light-cured, nano-filled desensitizer containing inorganic-organic hybrid polymer
(Ormocer) based preparation, such as Admira Protect, VOCO.

Phase 2—Caries, Leakage, Restauration, Indirect Pulp Capping

Reference is now made to internal use of the anti-inflammatory composition. The composition of the present invention may comprise materials used in dentistry after the etiology is removed. Non limiting examples of dental materials within the scope of the present invention, useful for internal application:
1. Radiopaque calcium Hydroxide Composition, such as Dycal, DENTSPLY.
2. Dentin-adhering liner and base material containing calcium hydroxide and calcium hydroxyapatite in a urethane dimethacrylate (UDMA) base composition, such as ULTRA-BLEND PLUS, ULTRADENT.
3. Light curing glass-ionomer cement, such as Vivaglass® Liner, IVOCLAR VIVADENT.
4. Vitrebond™ Plus Light Cure Glass Ionomer Liner/Base, 3M.

Phase 3—Continued Stimulus of the Dental Nerve: Direct Pulp Capping

Reference is now made to internal use of the anti-inflammatory composition. Non limiting examples of dental materials within the scope of the present invention, useful for direct pulp capping:
1. Radiopaque calcium Hydroxide Composition, such as Dycal, DENTSPLY ("The Golden standard").
2. Mineral trioxide aggregate, root canal repair material, such as ProRootMTA.

Phase 4—Intracanal Medication, Infected Stages

Reference is now made to intracanal application of the anti-inflammatory composition. Non limiting examples of dental materials within the scope of the present invention, useful for intracanal application:
1. Metapex-Calcium Hydroxide with Iodoform, such as META BIOMED.
2. Radiopaque, calcium hydroxide paste, such as Ultra-Cal® XS, ULTRADENT.
3. Demeclocycline hydrochloride and Triamcinolone acetonide, Ledermix paste, such as RIEMSER Pharma.

Phase 5—Periapical Periodontitis, Bone Defects and Dental Implant

Reference is now made to intrabone application of the anti-inflammatory composition. Non limiting examples of dental materials within the scope of the present invention, useful for intrabone application:
1. Bone substitute for regenerative dentistry Geistlich Bio-Oss®, GEISTLICH.
2 Platelet rich plasma (PRP).

EXPERIMENTAL DATA

CDB Solutions: Two CBD solutions were prepared at concentrations of 12.5% and 25% by dissolving CDB (as powder, 98% purity) in methanol to obtain the desired concentration.

Example 1

A 35 year old patent diagnosed with acute pulpitis with severe signs of pain on cold irritants, percussion pain with x-ray deep caries radiolucent areas adjacent to the coronal pulp. Hyperemia is evident in the dental canal system when opening of the coronal part of pulp chamber.

Pulpectomy (Removal of the entire pulp structure of a tooth, including the pulp tissue in the roots) was performed. The pulp was analyzed by phase contrast microscopy without staining.

Following Pulpectomy a solution of 0.1 ml CBD (25%) was applied for 1 min. A total reduction of bacteria's from the nerve fiber was observed.

The same application was made with a Clorhexidine gluconate 2% solution used in endodontics to rinse canal system of the roots. A reduction of less than 20% in bacteria's was observed.

Figure 6:
FIG. 6 is an X ray photograph of Patient 1, before treatment.

Histology slides prepared after pulpectomy of a second mandibular molar diagnosed with chronic irreversible pulpitis combined with periapical lesion (FIG. 6).

The treatment was performed with regular methods, in 2 steps 1 week rest. In the temporary dressing of the root canal medication Hydroxide Calcium was introduced 0.1 ml of CBD (25%) as well in the permanent sealer EWT Ken pulp sealer was introduced 0.5 ml of CBD (25%), pulp canal system sealed with sealer and gutta-percha.

Figure 7:
FIG. 7 is an X ray photograph of patient 1, 1 week after treatment.

After 1 week bone regeneration was identified by X-ray in the apical region see (FIG. 7). With standard treatment for periapical lesion, regeneration is usually noticed 6 months after treatment.

Figure 8:
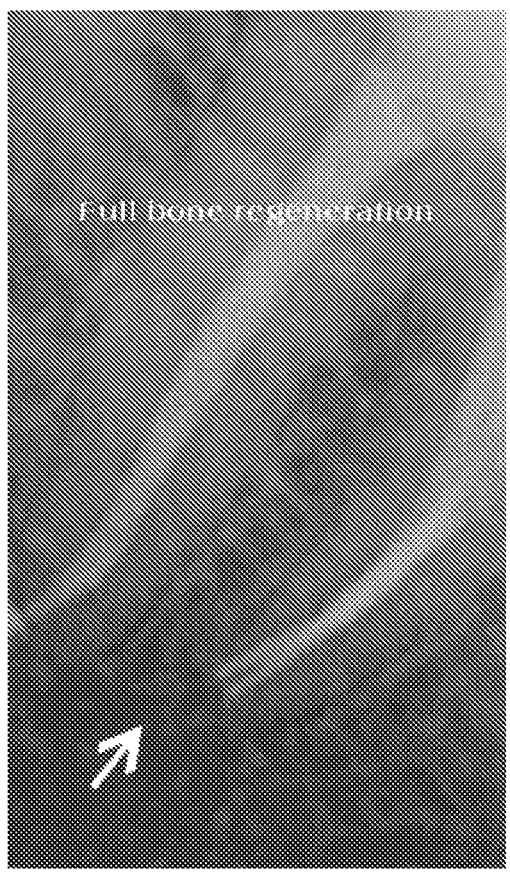
FIG. 8 is an X ray photograph of patient 1, 8 weeks after treatment.

Re-examination of the patient 8 weeks after treatment showed total regeneration (FIG. 8)

The pulp extract from the teeth was treated in-vitro and was sent to pathology lab. Pulp was extracted and separated to two samples:

Sample 1a was treated with 0.1 ml Clorhexidine Gluconate 2%.

Sample 1b was treated with solution of 0.1 ml CBD (25%) Results for sample 1a showed debris, bacteria, and enamel cement while the sample 1b showed connective tissue, bone and no bacteria.

This example shows the ability of a CDB dental preparation to treat bacterial infections and accelerate bone regeneration in a patient with acute pulpitis.

Example 2

Figure 9:
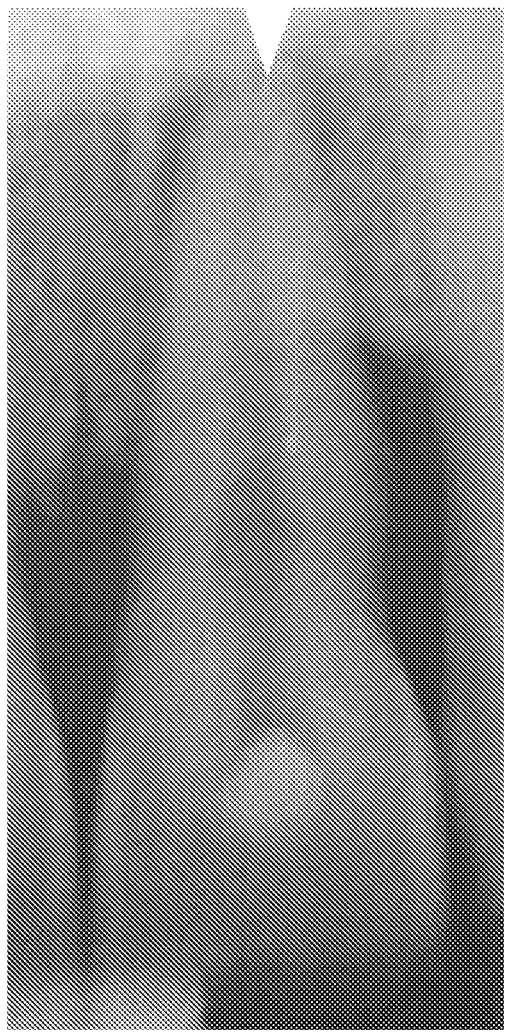
FIG. 9 is an X-ray photograph of patient 2, before treatment.

A 40 year old patient with a chronic Fistula in the region of the attached gingiva above the element 21 (FIG. 9). By opening the pulp chamber, canal hyperemia is evident, due to the high pressure in the canal even though the content is drained through the fistula.

Following cleaning and shaping, the canal was filled with a temporary pulp dressing with Ledermix paste, containing demeclocycline hydrochloride/triamcinolone acetonide, mixed with 0.1 ml CBD (25%) added to the composition.

1 week after the first treatment, the canal was rinsed and filled with EWT Ken pulp seal mixed with 0.1 ml CBD (25%).

Figure 10:
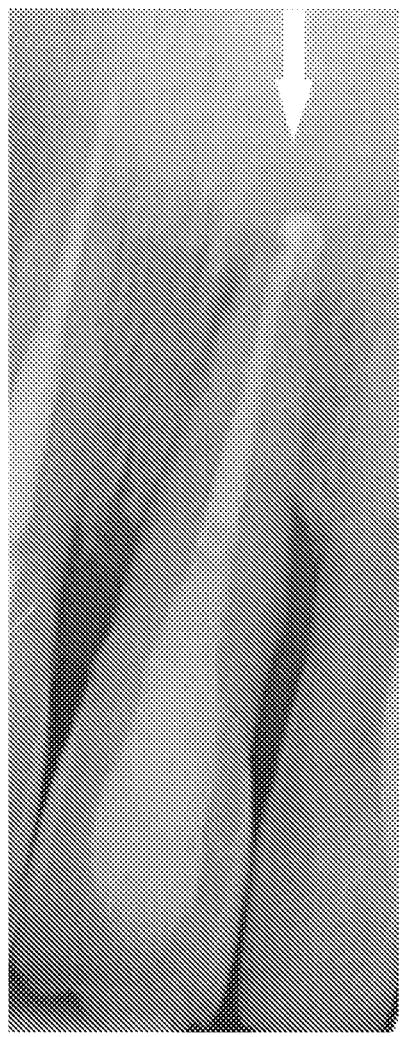
FIG. 10 is an X ray photograph of patient 2, 1 week after treatment.

2 weeks after the first treatment the canal was evaluated. Radiopacity and evident bone regeneration is evident (FIG. 10).

Two samples from the canal were isolated during cleaning, treated and sent to the pathology lab for analysis:

Sample 2a was treated with Ledermix

Sample 2b was treated with 0.1 ml CBD (25%)

The example shows that a formulation combining Ledermix with CBD has an improved effect on radiopacity and bone regeneration compared to standard Ledermix, as there is no evidence of inflammation cells or bacteria. Comparative radiopacity and bone regeneration commonly appears after 6 months.

Example 3

A 48 year old patient with chronic irreversible pulpitis element 28 wisdom tooth.

The element was hemisected and dental pulp extracted from tooth.

Sample 3a: Palatinal pulp was placed in Formalin.

Sample 3b: 0.1 ml CDB (25%) solution was applied to the vestibular canal pulp.

Sample 3b had no inflammation and no infection, as compared to 3a, showing the antibacterial effect of CBD in addition to the anti-inflammatory effect previously described.

Example 4

Samples of inflamed dental pulp and dental plaque were collected from various subjects and incubated at 37° C. for 24 hours The samples where then treated with CBD solutions (12.5% and 25%) and incubated for 5 min. The samples were stained with Dojindo Rapid staining kit BS02 and evaluated under a Cytation 5 cell imaging microscope.

Figure 11:
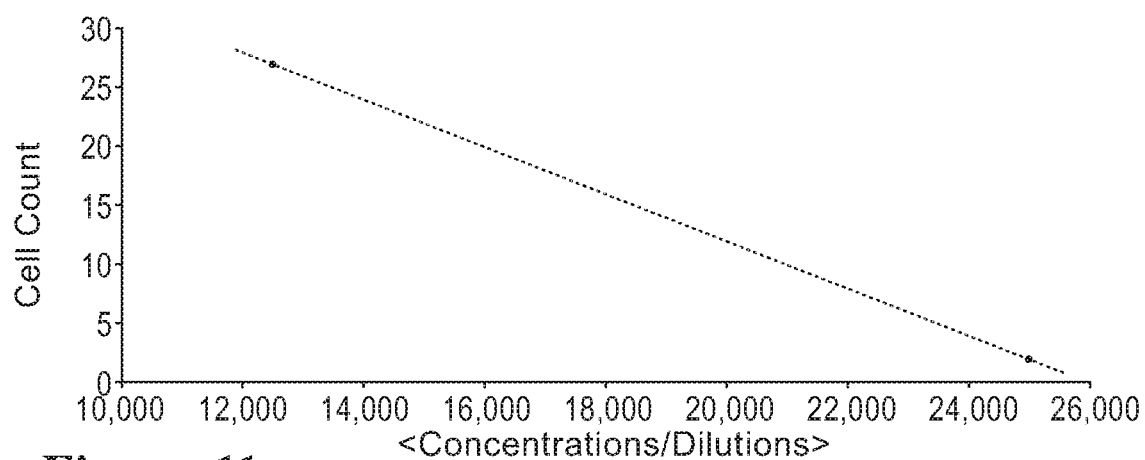
FIG. 11 is a graph showing the antibacterial activity of CBD.

FIG. 11 shows the anti-bacterial activity of the CDB solution, with an >75% reduction when treated with a 12.5% CBD solution and a >90% reduction when treated with a 25% CBD solution, in live bacterial cells as compared to an untreated sample.

Prevention of Dental Pulp Inflammation Conditions

The following is disclosed, providing proof of the efficacy of cannabinoid-based compositions of the present invention, for preventing dental pulp inflammation.

Patient A presented with periodontal inflammation, PDL enlargement, thermic sensitivity and some pain (the enlargement is clearly seen in FIG. 12A of 01.16.18).

The patient's inflamed gum region was treated daily by a local swabbed application of CBD oil 25%+1% THC for 1 week at the tooth neck zone.

A follow up examination was made approximately 8 months after the treatment (see FIG. 12B, 08.08.18).

Reduced PDL enlargement was observed and no thermic sensitivity was reported by patient. The dentist determined that, in view of the evidence, cannabinoid-based compositions useful for preventing dental pulp inflammation and reducing gum inflammation.

The dentist further determined that, due to the preventative treatment, there was no need for devitalization of the tooth.

Patient B presented with inflammation and recession of marginal gum (see FIG. 13A). The gum was treated with CBD oil 25% and 1% THC daily for 1 week. The patient was re-examined 2 weeks after the treatment, determining that the inflammation was reduced in the gums and no sensitivity was reported by patient (FIG. 13B).

The results obtained from Patient A and Patient B are clear indications that the compositions of the present invention are efficacious for prevention as well as treatment of dental pulp and gum inflammatory conditions.

The invention claimed is:

1. A method for the prevention or treatment of dental pulp associated diseases in a subject suffering therefrom, said method comprises the step of administering to the subject an effective amount of a cannabinoid-based composition comprising at least one of a natural or a synthetic cannabinoid,
    wherein prevention or treatment of dental pulp associated diseases comprises a reduction of live bacteria,
    wherein said dental pulp associated diseases comprise dental bone defects, wherein said dental bone defects are selected from the group consisting of dental jaw bone defects, disruption of the alveolar bone, osseous defects, concavities or deformities in the alveolar bone, bone loss, furcation involvement, inflammation, destruction of the supporting tissues by bacterial toxins and enzymes, one wall defect, two wall defect, crater defects, interdental crater defects, three wall defect, fenestration, dehiscence, bone destruction, lesion, interradicular bone defects or destruction, implant integration, and any combination thereof, and
    wherein said natural or a synthetic cannabinoid is at least one of CBD (Cannabidiol), CDB (Cannabigerol), a derivative thereof, a predefined ratio of a combination thereof.

2. The method according to claim 1, wherein said step of administering comprises administering via at least one of coronal, topical, intra pulpal, apical, periapical, intra canal, intra bone, intra apical foramen administration routes.

3. The method according to claim 1, wherein said method comprises a step of administering the effective amount of a cannabinoid-based composition in combination with a material, ingredient or composition conventionally used in dentistry.

4. The method according to claim 3, wherein said material, ingredient or composition conventionally used in dentistry is selected from the group consisting of: materials adapted to seal dental tubules such as glutaraldehyde and light-cured, nano-filled desensitizer containing inorganic-organic hybrid polymer (Ormocer) based preparation, radiopaque calcium Hydroxide, Dentin-adhering liner, base material containing calcium hydroxide and calcium hydroxyapatite in a urethane dimethacrylate (UDMA) base composition, light curing glass-ionomer cement, Vitrebond Plus Light Cure Glass Ionomer Liner/Base, Radiopaque calcium Hydroxide composition, root canal repair material such as mineral trioxide aggregate, Calcium Hydroxide with Iodoform such as Metapex, Radiopaque calcium hydroxide paste, Demeclocycline hydrochloride, Triamcinolone acetonide, bone substitute for regenerative dentistry, platelet rich plasma (PRP) and any combination thereof.

5. The method according to claim 3, wherein said cannabinoid-based composition confers a synergistic effect with respect to treatment or prevention of dental pulp inflammation and pain and/or dental bone defects as compared to the effect conferred by said cannabinoid-based composition and said material, ingredient or composition conventionally used in dentistry, administered separately.

6. A method for the prevention or treatment of dental pulp associated diseases in a subject suffering therefrom, said method comprises the step of administering to the subject an effective amount of a cannabinoid-based composition comprising at least one of a natural or a synthetic cannabinoid,
wherein prevention or treatment of dental pulp associated diseases comprises a reduction of live bacteria,
wherein said dental pulp associated diseases comprise dental bone defects,
wherein said treatment or prevention comprises at least one of: odontoblast vitality, dentin neoformation, reparative dentine formation, caries prevention, symptomatic/ asymptomatic pulpitis treatment, reversible pulpitis treatment, irreversible pulpitis treatment and prevention, acute pulpitis prevention and treatment, chronic pulpitis prevention and treatment, pulp necrosis prevention and treatment, bone building, reducing intra pulpal or intra canal pressure, improving implant therapy success, elimination of the periodontal lesion, osteogenesis, osteoinduction, osteoconduction, plaque control, bone formation, periodontal regeneration, induction of bone regeneration, osseous repair, guided tissue regeneration (GTR), implant integration stimulation, and wherein said natural or a synthetic cannabinoid is at least one of CBD (Cannabidiol), CBG (Cannabigerol), a derivative thereof, a predefined ratio of a combination thereof.

7. The method according to claim 1, wherein said natural or synthetic cannabinoid or a derivative thereof is selected from the group consisting of: CBD (Cannabidiol), CBDA (Cannabidiolic Acid), CBG (Cannabigerol), CBC (Cannabichromene), CBL (Cannabicyclol), CBV (Cannabivarin), CBDV (Cannabidivarin), CBCV (Cannabichromevarin), CBGV (Cannabigerovarin), CBGM (Cannabigerol Monomethyl Ether), Cannabielsoin (CBE), Cannabinol (CBN), Cannabinodiol (CBND), Cannabitriol (CBT) and any combination thereof.

8. A method for the prevention or treatment of dental pulp associated diseases in a subject suffering therefrom, said method comprises the step of administering to the subject an effective amount on a cannabinoid-based composition comprising at least one of a natural or a synthetic cannabinoid,
wherein prevention or treatment of dental pulp associated diseases comprises a reduction of live bacteria,
wherein said dental pulp associated disease comprises dental bone defects,
wherein said natural or a synthetic cannabinoid is at least one of CBD (Cannabidiol), CBG (Cannabigerol), a derivative thereof, a predefined ratio of a combination thereof, and wherein said step of administering an effective amount of a cannabinoid-based composition comprises at least one of the following steps:
(i) coronal application of the composition in an amount effective for odontoblast vitality and dentine neoformation;
(ii) coronal or intrapulpal application of the composition in an amount effective for treatment of caries penetrating the dentin and/or pulpitis;
(iii) intrapulpal application of the composition in an amount effective for treatment of irreversible pulpitis;
(iv) intrabone or apical foramen application of the composition in an amount effective for treatment of a pulp inflammation related condition selected from the group consisting of acute pulpitis, chronic pulpitis and pulp necrosis;
(v) intrabone injection or application of the composition in an amount effective for treatment of apical periodontitis; and
(vi) intrabone injection or application into the defected site and/or implantation bone site of the composition in an amount effective for dental bone defects treatment and/or implant integration stimulation.

9. The method according to claim 6, wherein said natural or synthetic cannabinoid or a derivative thereof are selected from the group consisting of: CBD (Cannabidiol), CBDA (Cannabidiolic Acid), CBG (Cannabigerol), CBC (Cannabichromene), CBL (Cannabicyclol), CBV (Cannabivarin), CBDV (Cannabidivarin), CBCV (Cannabichromevarin), CBGV (Cannabigerovarin), CBGM (Cannabigerol Monomethyl Ether), Cannabielsoin (CBE), Cannabinol (CBN), Cannabinodiol (CBND), Cannabitriol (CBT) and any combination thereof.

10. The method according to claim 8, wherein said natural or synthetic cannabinoid or a derivative thereof are selected from the group consisting of: CBD (Cannabidiol), CBDA (Cannabidiolic Acid), CBG (Cannabigerol), CBC (Cannabichromene), CBL (Cannabicyclol), CBV (Cannabivarin), CBDV (Cannabidivarin), CBCV (Cannabichromevarin), CBGV (Cannabigerovarin), CBGM (Cannabigerol Monomethyl Ether), Cannabielsoin (CBE), Cannabinol (CBN), Cannabinodiol (CBND), Cannabitriol (CBT) and any combination thereof.

* * * * *